United States Patent
Dearn

(10) Patent No.: US 6,649,659 B1
(45) Date of Patent: Nov. 18, 2003

(54) ATOVAQUONE PHARMACEUTICAL COMPOSITIONS

(75) Inventor: Alan Roy Dearn, Dartford (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 930 days.

(21) Appl. No.: 09/411,381

(22) Filed: Oct. 4, 1999

Related U.S. Application Data

(62) Division of application No. 08/974,248, filed on Nov. 19, 1997, now Pat. No. 6,018,080, which is a continuation of application No. 08/448,370, filed on May 31, 1995, now abandoned.

(30) Foreign Application Priority Data

Dec. 24, 1992 (GB) .............................................. 9226905

(51) Int. Cl.[7] ...................... A61K 31/122; C07C 49/83; C07C 49/115
(52) U.S. Cl. ....................................... 514/682; 568/328
(58) Field of Search ........................... 568/328; 514/682

(56) References Cited

U.S. PATENT DOCUMENTS

| | | |
|---|---|---|
| 2,533,648 A | 5/1950 | Fieser et al. |
| 3,347,830 A | 10/1967 | Rogers |
| 3,367,742 A | 2/1968 | Sarett |
| 4,107,288 A | 8/1978 | Oppenheim et al. |
| 4,783,389 A | 11/1988 | Trout et al. |
| 4,963,367 A | 10/1990 | Ecanow |
| 4,981,874 A * | 1/1991 | Latter et al. ................. 514/682 |
| 4,990,640 A | 2/1991 | Tsutsui et al. |
| 5,053,418 A | 10/1991 | Latter et al. |
| 5,053,432 A | 10/1991 | Hudson et al. |
| 5,155,080 A | 10/1992 | Elder et al. |
| 5,175,319 A | 12/1992 | Hudson et al. |
| 5,206,268 A | 4/1993 | Latter et al. |
| 5,225,184 A | 7/1993 | Latter et al. |
| 5,225,500 A | 7/1993 | Elder et al. |
| 5,310,762 A | 5/1994 | Latter et al. |
| 5,321,106 A | 6/1994 | LaPointe |
| 5,322,902 A | 6/1994 | Schreck et al. |
| 5,387,568 A | 2/1995 | Ewen et al. |
| 5,510,118 A | 4/1996 | Bosch et al. |
| 5,766,522 A | 6/1998 | Daly et al. |
| 5,914,135 A * | 6/1999 | Dubek et al. ................ 424/687 |
| 5,976,578 A * | 11/1999 | Beyerle et al. ............. 424/686 |

FOREIGN PATENT DOCUMENTS

| | | |
|---|---|---|
| EP | 0 002 228 B1 | 6/1979 |
| EP | 0 077 550 B1 | 4/1983 |
| EP | 0 077 551 A2 | 4/1983 |
| EP | 0 123 239 A2 | 10/1984 |
| EP | 0 362 996 A2 | 4/1990 |
| EP | 0 426 638 | 5/1991 |
| EP | 0 427 697 | 5/1991 |
| GB | 1 141 735 | 1/1969 |
| GB | 1 268 316 | 3/1972 |
| GB | 1 533 424 | 9/1979 |
| JP | 4-337308 | 11/1992 |
| WO | WO 88/05792 | 8/1988 |
| WO | WO 88 95793 | 8/1988 |

OTHER PUBLICATIONS

VIII International Conference on AIDS/III STD World Congress, Amsterdam, The Netherlands, Jul. 19–24, 1991, "Final Progran & Oral Abstracts".

SCRIP No. 1671, Nov. 22, 1991, pp. 24–25.

Young Taek Son et al. of The Korean Pharmacological Society, *Pharmacology*, Korean Pharmacological Society, §1. "Introduction—5.1 Efficacy, §5, Bioavailability—1.2 Physico–chemical Property of a Medicament Affecting Absorption," Published in Korea by by Moon Sung Sa, 98–31, Sinsul–dong, Dongdaemun–ku, Seoul, Korea (Mar. 20, 1991).

Wofsy, pp 377–401, Chapter 36, 1986.

Fieser et al vol. 70 pp. 3156–3165, 1948.

Hughs, Parasitology Today, vol. 3, No. 11, pp. 332–335, 1887.

Parsons, 10 pages, issued Aug. 7, 1989.

Discriminant Analysis and Structure–Activity Relationships 1. Naphthoquinone; J. Med. Chem. vol. 21; No. 4, 1978; pp. 369–374.

Role of the Naphthoquinone Moiety in the Biological Activities of Sakyomicin A. J. Antibiot., vol. 39, No. 4; 1986; pp. 557–563.

Inhibition of Thioredoxin Reductase (E.C. 1.6.4.5) by Antitumo Quinones; Free Rad. Res. Commun. vol. 8; No. 4–6; 1990; pp 365–372.

* cited by examiner

*Primary Examiner*—Barbara P. Badio
(74) *Attorney, Agent, or Firm*—Nixon & Vanderhye P.C.

(57) ABSTRACT

The invention relates to a process for the production of microfluidized particles of atovaquone having improved bioavailability.

12 Claims, No Drawings

ATOVAQUONE PHARMACEUTICAL COMPOSITIONS

This is a division of application Ser. No. 08/974,248, filed Nov. 19, 1997, now U.S. Pat. No. 6,018,080 which is a continuation of Ser. No. 08/448,370, filed May 31, 1995 now abandoned, the entire content of which is hereby incorporated by reference in this application.

The present invention relates to microfluidised particles of 2-[4-(4-chlorophenyl) cyclohexyl]-3-hydroxy-1,4-naphoquinone and to a method for preparing then. More particularly the invention is concerned with a pharmaceutical composition containing microfluidised particles of 2-[4-(4-chlorophenyl)cyclohexyl]-3-hydroxy-1,4-naphthoquinone ("atovaquone") and its use in therapy.

Atovaquone has previously been disclosed, for example in European Patent No. 0123238 and U.S. Pat. No. 5,053,432 (incorporated herein by reference) which relates to 2-substituted-3-hydroxy-1,4-naphthoquinones of formula (I):

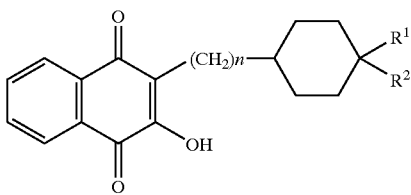

wherein either $R^1$ is hydrogen and $R^2$ is selected from C alkoxy, aralkoxy, $C_{1-6}$ alkyl-$C_{1-6}$ alkoxy, phenyl substituted by one or two groups selected from halogen and $C_{1-6}$ alkyl, halogen and perhalo-$C_{1-6}$ alkyl or $R^1$ and $R^2$ are both C alkyl or phenyl, and n is zero or 1, and physiologically acceptable salts thereof. The compounds are said to have antiprotozoal activity. Specifically, compounds of formula (I) wherein n is zero are said to be active against the human malaria parasite *Plasmodium falciparum* and also against *Eimeria* species such as *E. tenella* and *E. acervulina*, which are causative organisms of coccidiosis and compounds of formula (I) where n is 1are said to be active against protozoa of the As Theileria, in particular T. annulata or T. parva. Amongst the compounds specifically named and exemplified is the compound of formula (I) wherein n is zero, $R^1$ is hydrogen and $R^2$ is 4-chlorophenyl, i.e. atovaquone.

EP 0362996 discloses the use of atovaquone in the treatment and/or prophylaxis of *Pneumocystis carinii* pneumonia.

Further uses of atovaquone against Toxoplasmosis and Cryptosporidiosis are disclosed in European patent application nos. 0445141 and 0496729 respectively.

The efficacy of atovaquone as a therapeutic agent is limited by its bioavailability. Accordingly it is an object of the present invention to provide atovaquone in a more bioavailable form.

It has now been found that the bioavailability of atovaquone can be increased by ensuring that the particle size is within a certain defined range of small particles. However, conventional methods of reducing the particle size of atovaquone were found to be unsuccessful in producing particles of the size required to improve bioavailability.

The Microfluidiser has been marketed by the Microfluidics Corporation since 1985. The principle of its operation is based on a submerged jet technology. It was designed, primarily, as a homogenizing device for use in the food and pharmaceutical industries, for the preparation of e.g. emulsion and liposomal systems and has subsequently been used for cell-rupture purposes in biotechnology applications.

It has now surprisingly been found that microfluidised particles of atovaquone produced using a Microfluidiser have improved bioavailability of the compound. It is believed that this is due to the small size and narrow range of sizes of the microfluidised atovaquone particles.

During operation of the Microfluidiser, the feed stream is pumped into a specially designed chamber, in which fluid streams interact at very high velocities and pressures. Fixed microchanels within the interaction chamber provide an extremely focussed interaction zone of intense turbulence, causing the release of energy amid cavitation and shear forces. Without wishing to be bound by theory it is believed that since all product passes through a dimensionally fixed area of energy release, greater size uniformity and smaller sizes are achieved by using the Microfluidiser rather than conventional methods for producing fine particles.

Thus, in a first aspect, the present invention provides small particles of atovaquone. Preferably the particles are microfluidised particles. Suitably at least 90% of the particles have a volume diameter in the range of 0.1–3$\mu$m. Preferably at least 95% of the particles have a volume diameter in the range 0.1–2$\mu$m.

In a second aspect, the present invention provides a pharmaceutical composition comprising particles of atovaquone and one or more pharmaceutically acceptable carriers therefore wherein at least 95% of the particles have a volume diameter in the range of 0.1–2$\mu$m. Preferably the particles are microfluidised particles.

The carriers must be acceptable in the sense of being compatible with the other ingredients of the formula and not deleterious to the recipient thereof According to a third aspect the present invention provides a method for the preparation of microfluidised particles of atovaquone which comprises mixing atovaquone with a liquid vehicle to provide a mixture wherein the concentration of atovaquone is less than 450mg/mL and subjecting said mixture to at least 3 passes through a Microrfluidiser in order to provide the atovaquone in the form of particles wherein at least 90% of the particles have a volume diameter in the range 0.1–3$\mu$m. Preferably at least 95% of the particles have a volume diameter in the range 0–1–2$\mu$m.

In a further aspect the present invention provides a method for the preparation of a pharmaceutical composition comprising the steps of:

a) mixing atovaquone with a liquid vehicle to provide a mixture wherein the concentration of atovaquone is less than 450mg/mL.

b) subjecting the mixture to at least 3 passes through a Microfluidiser to provide a microfluidised preparation wherein the atovaquone is in the form of particles and at least 95% of those particles have a volume diameter in the range 0.1–2$\mu$m.

c) mixing the microfluidised preparation with one or more pharmaceutically acceptable carriers therefor.

Suitably, the mixture is subjected to 10–50 passes through the Microfluidiser, e.g. 25–30 passes. Preferably the mixture is subjected to 15–25 passes through the Microfluidiser.

In one embodiment, the liquid vehicle is a surfactant. Preferably, the liquid vehicle is a surfactant solution. In a particularly preferred embodiment the surfactant is Poloxamer 188 solution. In another preferred embodiment the pharmaceutically acceptable carriers include a suspending agent. Suitable suspending agents include methyl cellulose and xanthan gum. Preferably the suspending agent is xanthan gum.

Pharmaceutical formulations include those suitable for oral and parenteral (including subcutaneous, intradermal intramuscular and intravenous) administration as well as administration by naso-gastric tube. Suitable formulations within the scope of the present invention include, for example, solid dosage forms such as tablets and liquid dosage forms, such as suspensions, which are preferred formulations. The formulation may, where appropriate, be conveniently presented in discrete dosage units and may be prepared from the microfluidised particles using methods known in the art of pharmacy.

Tests to measure the bioavailability of atovaquone in vivo indicate that formulations of microfluidised atovaquone have improved bioavailability compared to prior art formulations. The invention therefore provides, in a further aspect, formulations comprising microfluidised atovaquone for use in therapy, in particular in the treatment and prophylaxis of protozoal parasitic infections, e.g. malaria and toxoplasmosis, and infections caused by P. carinii.

The invention will now be further illustrated by the following non-limiting examples:

EXAMPLE 1

Preparation of Microfluidised Particles of Atovaquone

Atovaquone was prepared by methods according to the prior art, e.g. U.S. pat. No. 5,053,432 (incorporated herein by reference). 600 mL of a mixture consisting of 2.5% w/v atovaquone in 0.25% w/v aqueous Celacol M2500 was prepared and 100 mL were retained in a glass jar as a control. A laboratory scale model 120B Microfluidiser was connected to a 90 psi pneumatic supply and adjusted to produce a fluid pressure of 15000 psi. The machine base, interaction chamber and pipework of the Microfluidiser were immersed in a bath of cold water. 500 mL of the mixture were loaded into the Microfluidiser's bulk vessel and passed through the Microfliudiser interaction chamber before being returned to the top, and side, of the bulk chamber. The mixture was recirculated continuously through the interaction chamber, and samples were taken at 10, 20, 30, 45 and 60 minutes. The number of passes to which each of these samples had been subjected was calculated and is shown in Table 1 below.

TABLE 1

| Sample | Microfluidisation time (minutes) | Sample Volume (ml) | Number of passes |
|---|---|---|---|
| Control | 0 | 100 | 0 |
| 1 | 10 | 105 | 8 |
| 2 | 20 | 105 | 9–19 |
| 3 | 30 | 110 | 31–35 |
| 4 | 45 | 105 | 65–77 |
| 5 | 60 | 35 | 142–244 |

Microscopic observations of the control and samples at 40x magnification were made and the results were as follows:

| | |
|---|---|
| Control | Varied shapes, plates, rods and spheroids, around 5 × 5 $\mu$m generally and up to 7.5 × 10 $\mu$m, loosely aggregated. |
| Sample 1 | More rounded smaller shapes, some "large" crystals, lots of small fragments 2.5 × 2.5 $\mu$m, more dispersed. |
| Sample 2 | More rounded, smaller shapes, more fragments. |
| Sample 3 | Still more rounded, smaller shapes, more fragments. |
| Sample 4 | Yet more rounded, smaller shapes, more fragments. |
| Sample 5 | Very small particles, all under 2.5 $\mu$m, all rounded, monodisperse. |

EXAMPLE 2

Pharmaceutical Formulation

An oral suspension formulation was prepared by the following ingredients:

| | |
|---|---|
| Microfluidised particles of atovaquone | 150.0 mg |
| Poloxamer 188 | 5.0 mg |
| Benzyl alcohol | 10.0 mg |
| Xanthan gum | 7.5 mg |
| Purified water to make | 1.0 mL |

EXAMPLE 3

Biological Test

Nine healthy fasted male volunteers received single doses of 5 mg/L suspensions containing 250 mg atovaquone as a 3 $\mu$m mean particle size suspension and 1 $\mu$m Microfluidised suspension in a randomised crossover study. Plasma samples were taken at intervals up to two after the last dose and assayed by HPLC. The results are given in table 2 below:

TABLE 2

| | 3 $\mu$m suspension | 1 $\mu$m suspension |
|---|---|---|
| mean(SD)AUC | 95 (62) $\mu$g/mL.h | 247(85) $\mu$g/mL.h |
| mean(SD)$C_{max}$ | 1.2(0.7) $\mu$g/mL | 5.0(1.6) $\mu$g/mL |
| median $T_{max}$ | 5 hours | 1 hour |

The mean (95% CI) increase for the AUC of the 1$\mu$m suspension relative to the 3$\mu$m suspension was 2.6-fold (1.9–3.5) and for $C_{max}$ was 4.1-fold (2.5–6.6).

What is claimed is:

1. Small particles of atovaquone wherein at least 90% of the particles of atovaquone have a volume diameter in the range 0.1–3 $\mu$m.

2. Small particles of atovaquone wherein the particles of atovaquone have been microfluidized.

3. Microfluidized particles of atovaquone wherein at least 90% of the microfluidized particles of atovaquone have a volume diameter in the range 0.1–3 $\mu$m.

4. A pharmaceutical composition comprising particles of atovaquone and one or more pharmaceutically acceptable carriers therefor wherein at least 90% of the particles have a volume diameter in the range of 0.1–3 $\mu$m.

5. A pharmaceutical composition according to claim 4, wherein the particles are Microfluidized particles.

6. A pharmaceutical composition according to claim 4 or claim 5 in suspension.

7. A pharmaceutical composition according to claim 4 wherein the pharmaceutically acceptable carriers include a suspending agent.

8. A pharmaceutical composition according to claim 4 in suspension wherein the pharmaceutically acceptable carriers include a suspending agent.

9. A pharmaceutical composition according to claim 7, wherein the suspending agent is xanthan gum.

10. A pharmaceutical composition according to claim 8, wherein the suspending agent is xanthan gum.

11. A method for the treatment and/or prophylaxis of protozoal infections in mammals which comprises administering to said mammals an effective amount of particles of atovaquone and one or more pharmaceutically acceptable carrier therefor wherein at least 90% of the particles have a volume diameter in the range of 0.1–3 µm.

12. The method according to claim 11 wherein said protozoal infection is caused by *Pneumocystis carinii*.

* * * * *